United States Patent
Hayworth

(10) Patent No.: US 9,353,585 B2
(45) Date of Patent: May 31, 2016

(54) ON-THE-FLY ACID BLENDER WITH SAMPLING EQUIPMENT

(75) Inventor: Robert Hayworth, Chickasha, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 488 days.

(21) Appl. No.: 13/195,624

(22) Filed: Aug. 1, 2011

(65) Prior Publication Data

US 2011/0284220 A1 Nov. 24, 2011

Related U.S. Application Data

(63) Continuation-in-part of application No. 12/044,228, filed on Mar. 7, 2008, now abandoned.

(51) Int. Cl.
*E21B 21/10* (2006.01)
*E21B 34/00* (2006.01)
(Continued)

(52) U.S. Cl.
CPC ........... *E21B 21/062* (2013.01); *B01F 15/0416* (2013.01); *E21B 43/267* (2013.01);
(Continued)

(58) Field of Classification Search
CPC ... E21B 2034/007; E21B 34/14; E21B 34/12; E21B 43/12; E21B 34/06; E21B 34/063; E21B 34/00; E21B 21/10; E21B 21/106; E21B 23/08
USPC ........... 166/344, 345, 351, 373, 90.1; 175/65, 175/206, 207; 137/88, 98, 100, 101.19, 137/111, 114
See application file for complete search history.

(56) References Cited

U.S. PATENT DOCUMENTS 2,039,816 A * 5/1936 Lupfer .................... E21B 3/02
173/151
3,109,631 A * 11/1963 Purjahn .................. B01F 5/045
366/152.2

(Continued)

FOREIGN PATENT DOCUMENTS

| EP | 0630728 | 12/1994 |
| EP | 0665050 | 8/1995 |
| EP | 0845291 | 3/1998 |

OTHER PUBLICATIONS

Kevin Cook, Existing Process Sampling Methods & New Sampling Devices for the Process Industry, Fall 2001.
(Continued)

*Primary Examiner* — Matthew R Buck
*Assistant Examiner* — Edwin Toledo-Duran
(74) *Attorney, Agent, or Firm* — John W. Wustenberg; Baker Botts L.L.P.

(57) ABSTRACT

A method for blending a well treatment fluid at a well site is disclosed. A first centrifugal pump for pumping a first component of the well treatment fluid into a pipe and a first valve for controlling the flow of the first component are provided. Similarly, a second centrifugal pump for pumping a second component of the well treatment fluid into the pipe and a second valve for controlling the flow of the second component are provided. The pumps and the valves are controlled so as to control the ratio of the first component to the second component. A sampling device is provided for analyzing a fluid flowing in the pipe. The sampling device includes a sampling container; a soft seal that opens and closes the sampling container; and a valve spindle. The valve spindle moves the soft seal between the first position and the second position.

20 Claims, 5 Drawing Sheets

(51) Int. Cl.
  *E21B 21/06*   (2006.01)
  *B01F 15/04*   (2006.01)
  *E21B 43/267*  (2006.01)
  *G01N 1/20*    (2006.01)

(52) U.S. Cl.
  CPC ........ *G01N1/2035* (2013.01); *G01N 2001/205* (2013.01); *G01N 2001/2064* (2013.01); *G01N 2001/2071* (2013.01)

(56) References Cited

U.S. PATENT DOCUMENTS

| | | | | |
|---|---|---|---|---|
| 3,326,536 | A * | 6/1967 | Zingg | B01F 5/22 366/17 |
| 3,817,658 | A * | 6/1974 | Murase | G05D 11/131 137/7 |
| 3,902,558 | A * | 9/1975 | Watson, Jr. | E21B 43/20 166/275 |
| 4,454,773 | A * | 6/1984 | Brunner | E21B 49/086 141/236 |
| 4,929,088 | A * | 5/1990 | Smith | B01F 5/0473 138/40 |
| 7,740,708 | B2 * | 6/2010 | Lofton | B08B 9/0321 134/22.1 |
| 2004/0007392 | A1 * | 1/2004 | Judge | E21B 21/001 175/206 |
| 2005/0006089 | A1 * | 1/2005 | Justus | E21B 43/267 166/250.01 |
| 2009/0007650 | A1 * | 1/2009 | Hayworth | E21B 47/10 73/152.29 |

OTHER PUBLICATIONS

NeoTecha Safety Cabinet with Adapter, May 17, 2004.
Tyco Flow Control, NeoTecha In-Line Sampling System—Sapro, 2007.
International Search Report and Written Opinion for PCT/GB2009/000606, Dated September 24, 2009.
Office Action issued in U.S. Appl. No. 12/044,228, Jun. 14, 2011.
Office Action issued in U.S. Appl. No. 12/044,228, Feb. 7, 2011.
U.S. Appl. No. 11/673,290, filed Feb. 9, 2007, Dant.

* cited by examiner

ON-THE-FLY ACID BLENDER WITH SAMPLING EQUIPMENT

This application is a continuation-in-part of U.S. patent application Ser. No. 12/044,228 filed on Mar. 7, 2008, now abandoned and claims priority to that application pursuant to 35 U.S.C. §120.

BACKGROUND

On-the-fly blending of well treatment fluids is not typically used for corrosive chemicals. Generally, blending corrosive chemicals, otherwise known as acids, or hazardous chemicals, is done at a location other than the well site, using batch mixing. The chemicals are mixed in a tank at a bulk chemical plant and then transported to the well site. The mixing and the transportation are costly. Specialized transports are required to transport the mix. Additionally, specially trained personnel are required. In addition to being costly, this can be undesirably time consuming. Further, any real-time change to the mix presents problems, as an entire new batch must be mixed and transported. While this occurs, the job must wait, which can be extremely costly. Further, batch mixing requires that the tank be emptied prior to changing the mix. It is difficult to anticipate the exact amount of mix that will be required for a given application. This generally leads to excess mix left in the tank at the end of a job, or at a change point. Proper disposal of this mix can be environmentally hazardous, costly, and dangerous.

Additionally, for on-the-fly blending of acids to be successful, the flow and pressure of the different components must be controlled. For instance, a good blend cannot be obtained if one fluid component flows at 60 psi and another at 20 psi. Additionally, it is important for the base fluid (e.g. water) not to enter the raw acid. Accordingly, it is important to be able to control the different components in order to prepare the mixture in a prescribed order.

Moreover, it is important to monitor the properties of a treatment fluid to ensure proper performance. Traditionally, a valve and bucket approach is used to take a sample of the treatment fluid out of the system for testing and analysis. Specifically, the onsite personnel would have to open a valve and obtain a sample of the treatment fluid in a bucket for analysis. However, the traditional methods of retrieving samples have several drawbacks. The treatment fluid often comprises hazardous, corrosive or flammable material thereby posing a danger to the equipment, environment and the personnel taking the sample. Moreover, exposure to elements can compromise the sample properties leading to inaccurate results when analyzing the sample.

FIGURES

Some specific example embodiments of the disclosure may be understood by referring, in part, to the following description and the accompanying drawings.

Figure 1:
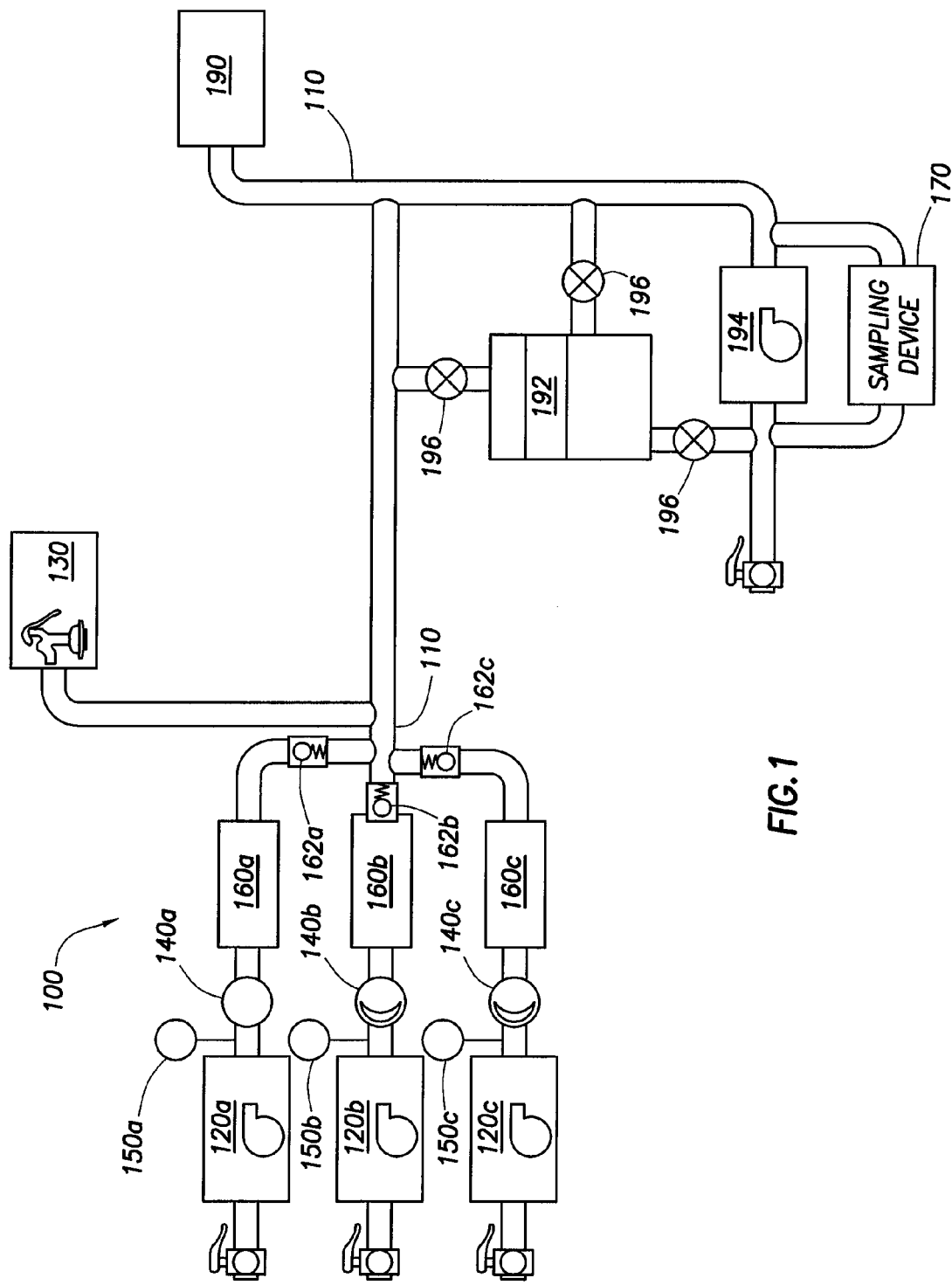
FIG. 1 is a system for on-the-fly blending of treatment fluids with a sampling device in accordance with an exemplary embodiment of the present invention.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

SUMMARY

The present invention is directed to blending fluids. Specifically, the present invention is directed to improved methods and systems of blending and analyzing well treatment fluids at a well site.

In one embodiment, the present invention is directed to a method for blending a well treatment fluid at a well site, comprising: providing a first centrifugal pump for pumping a first component of the well treatment fluid into a pipe; providing a first valve for controlling the flow of the first component of the well treatment fluid into the pipe; providing a second centrifugal pump for pumping a second component of the well treatment fluid into the pipe; providing a second valve for controlling the flow of the second component of the well treatment fluid into the pipe; controlling the pumps and the valves so as to control the ratio of the first component of the well treatment fluid to the second component of the well treatment fluid being delivered to the pipe; and providing a sampling device for analyzing the well treatment fluid.

In another embodiment, the present invention is directed to a system for blending a well treatment fluid at a well site, comprising: a first centrifugal pump for pumping a first component of the well treatment fluid into a pipe; a first valve for controlling the flow of the first component of the well treatment fluid into the pipe; a second centrifugal pump for pumping a second component of the well treatment fluid into the pipe; a second valve for controlling the flow of the second component of the well treatment fluid into the pipe; means for controlling the pumps and the valves so as to control the ratio of the first component of the well treatment fluid to the second component of the well treatment fluid being delivered to the pipe; and a sampling device for monitoring the well treatment fluid.

The features and advantages of the present disclosure will be readily apparent to those skilled in the art upon a reading of the description of exemplary embodiments, which follows.

DESCRIPTION

The present invention is directed to blending fluids. Specifically, the present invention is directed to improved methods and systems of blending and analyzing well treatment fluids at a well site.

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

An improved method of blending the components of a well treatment fluid is disclosed in patent application Ser. No. 11/673,290, filed Feb. 9, 2007, which is incorporated herein by reference in its entirety.

The terms "couple" or "couples," as used herein are intended to mean either an indirect or direct connection. Thus, if a first device couples to a second device, that connection may be through a direct connection, or through an indirect electrical connection via other devices and connections.

Referring now to FIG. 1, an exemplary embodiment of a system for preparing and analyzing acids on-the-fly at a desired rate is depicted generally with reference numeral 100. The system 100 blends various components of the well treatment fluid directly into a pipe 110. This reduces or eliminates the need for standard mixing tanks or tubs. This may be accomplished using at least two centrifugal pumps 120 (shown as 120a, 120b, and 120c). The centrifugal pumps 120 may each pump a different component of the desired well treatment fluid.

As would be appreciated by those of ordinary skill in the art, with the benefit of this disclosure, more than two centrifugal pumps may be used to allow for more than two different components to be mixed together. For example, in one embodiment the system may include three centrifugal pumps for an acid treatment, where a first centrifugal pump may pump a hazardous chemical such as hydrochloric acid ("HCl"), a second centrifugal pump may pump water, and a third centrifugal pump may pump a highly corrosive chemical such as Ammonium Bi-Fluoride ("AF"). While HCl, water, and AF are disclosed, it should be understood that the chemicals may include any acid, hazardous chemical, corrosive, or other fluid. For instance, in another exemplary embodiment a non-aqueous fluid may be used as a primary flow stream. In one embodiment, the non-aqueous fluid may include diesel.

The system 100 may also include one or more valves 140 (shown as 140a, 140b, and 140c) for controlling the flow of the various components from the centrifugal pumps 120 into the pipe 110. The valves 140 may be butterfly valves, or any other valve suitable for use with well treatment fluids.

Between the centrifugal pumps 120 and the valves 140, the system 100 may include one or more pressure transducers 150 (shown as 150a, 150b, and 150c) that act as pressure controls on the centrifugal pumps 120, preventing the centrifugal pumps 120 from pushing one another off line. Feedback from pressure transducers 150 may signal pressure set points in centrifugal pumps 120, such that the centrifugal pumps 120 maintain a desirable balance.

Between the valves 140 and the pipe 110, the system 100 may additionally include one or more flow meters 160 (shown as 160a, 160b, and 160c) and one or more check valves 162 (shown as 162a, 162b, and 162c) to monitor and control flow rates from the pumps 140.

Additional liquid additives may also be introduced into the pipe 110. The additives may be stored in liquid additive storage tanks (not shown), and pumped into the pipe 110 via one or more liquid additive pumps 130. In one exemplary embodiment, the liquid additive tanks may include a low-level warning system to notify a user when the level of a particular liquid additive falls below a preset threshold value. As would be appreciated by those of ordinary skill in the art, in one embodiment, the notification may be in the form of an audible alarm or strobe lights. This feature helps ensure that the required amount of the various materials needed at the well site is available for performance of the subterranean operation at hand.

While the liquid additive pump 130 is shown as a hand pump, the liquid additive pump 130 may be any type of pump, including, but not limited to, a positive displacement pump. One or more liquid additive valves (not shown) may be included to control the flow of liquid additives from the liquid additive pumps 130 into the pipe 110.

The well treatment fluid may be blended directly in the pipe 110, without the use of any tank. The flow rate and pressure of any of the components may be controlled by controlling the pumps 120 and 130 and the valves 140. This allows for the ratio of the various components and additives of the well treatment fluid to be modified as necessary for the specific field conditions at any given time. This modification can take place in real-time, allowing the desired well treatment fluid mix to be pumped into the well as it is needed.

Additionally, the system 100 may have a number of additional valves (not shown), with locations suitable for controlling flow in various ways as would be readily understood by one of ordinary skill in the art. For example, these additional valves may be butterfly valves, some of which are open and some of which are closed. In one exemplary embodiment, the additional valves may be used to address the mixing orders of some specific fluids by allowing a user to inject liquid additives into the raw product flow streams prior to entering the pipe 110.

A discharge flow meter 190 may be included in the system 100. This may allow for adjustments to be made to the pumps 120 and valves 140, such that the correct mix ratio is maintained without creating undesirable negative pressure in the system 100. After the mix has passed through the discharge flow meter 190, it may pass through another pump (not shown), which then pumps the mix downhole.

The system 100 may also optionally include a discharge recirculation pump 194. The discharge recirculation pump 194 may serve two purposes. The first may be for recirculation. The second may be for discharge at very low flow rates. The recirculation pump 194 may be any type of pump for discharge recirculation (e.g., a 120 HP pump).

A sampling device 170 may be coupled to the system 100. In one embodiment, the sampling device 170 may be coupled to the system in parallel to the discharge recirculation pump 194. The sampling device may allow the operator to take samples of the fluid produced by the system 100 while protecting personnel from exposure to the material flowing through the pipe 110 which is often comprised of hazardous chemicals.

Figure 2:
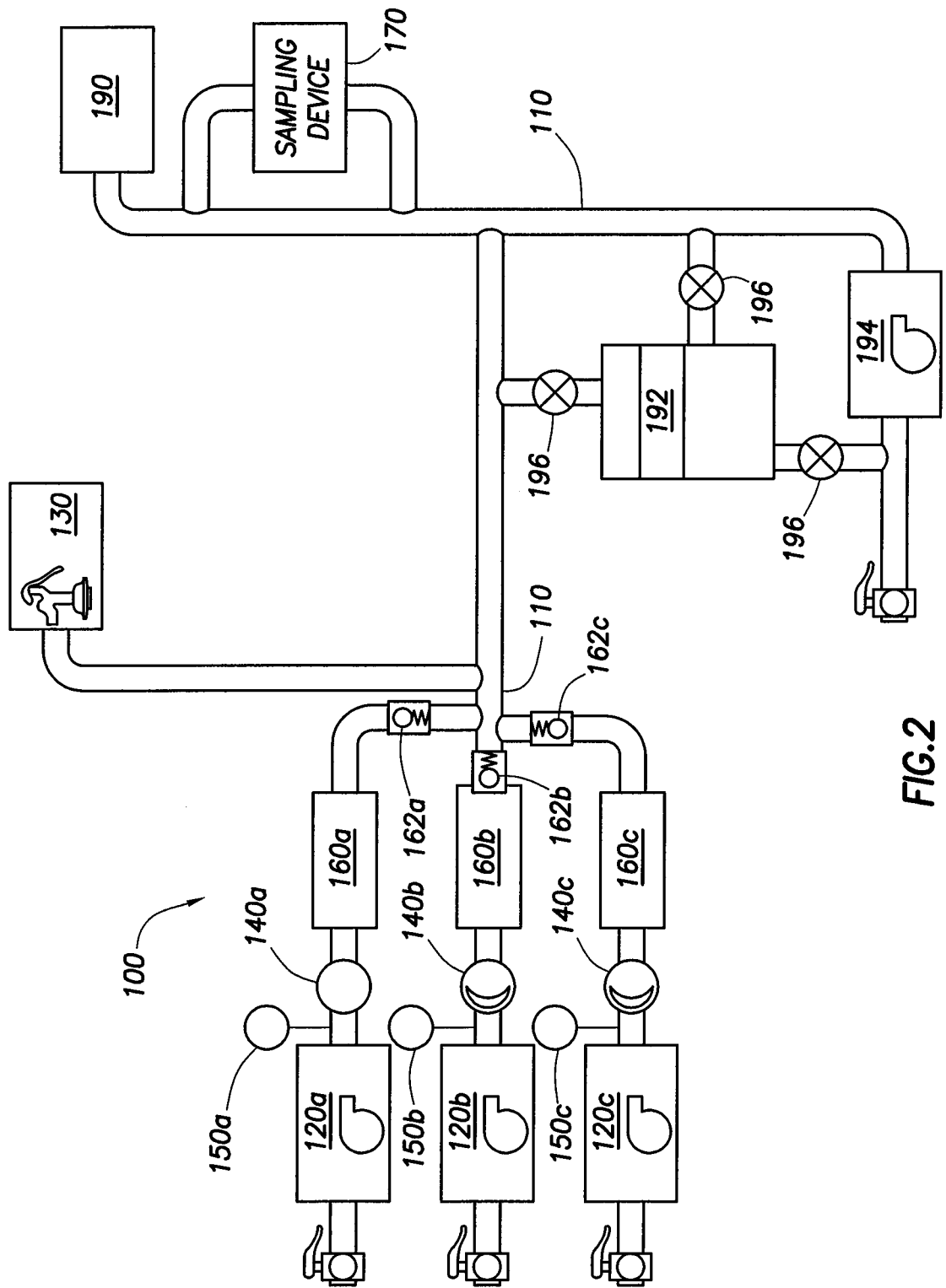
FIG. 2 is a system for on-the-fly blending of treatment fluids with a sampling device in accordance with another exemplary embodiment of the present invention.

FIG. 2 depicts another exemplary embodiment of the present invention where the sampling device 170 is coupled to the pipe 110 just before the fluid enters the discharge flow meter 190.

As would be appreciated by those of ordinary skill in the art, with the benefit of this disclosure, in one embodiment (not shown) the sampling device 170 may be removably coupled to the system 100. It may be desirable to attach the sampling device 170 to the system 100 when a sample is to be taken and remove it when the sampling process has been completed. One or more valves (not shown) may be used to control the fluid flow through the sampling device 170. The valves may be closed when no sample is to be taken or when the sampling device 170 is not coupled to the system 100. Once the operator decides to take a sample the valves may be opened to allow fluid flow through the sampling device 170.

Figure 3:
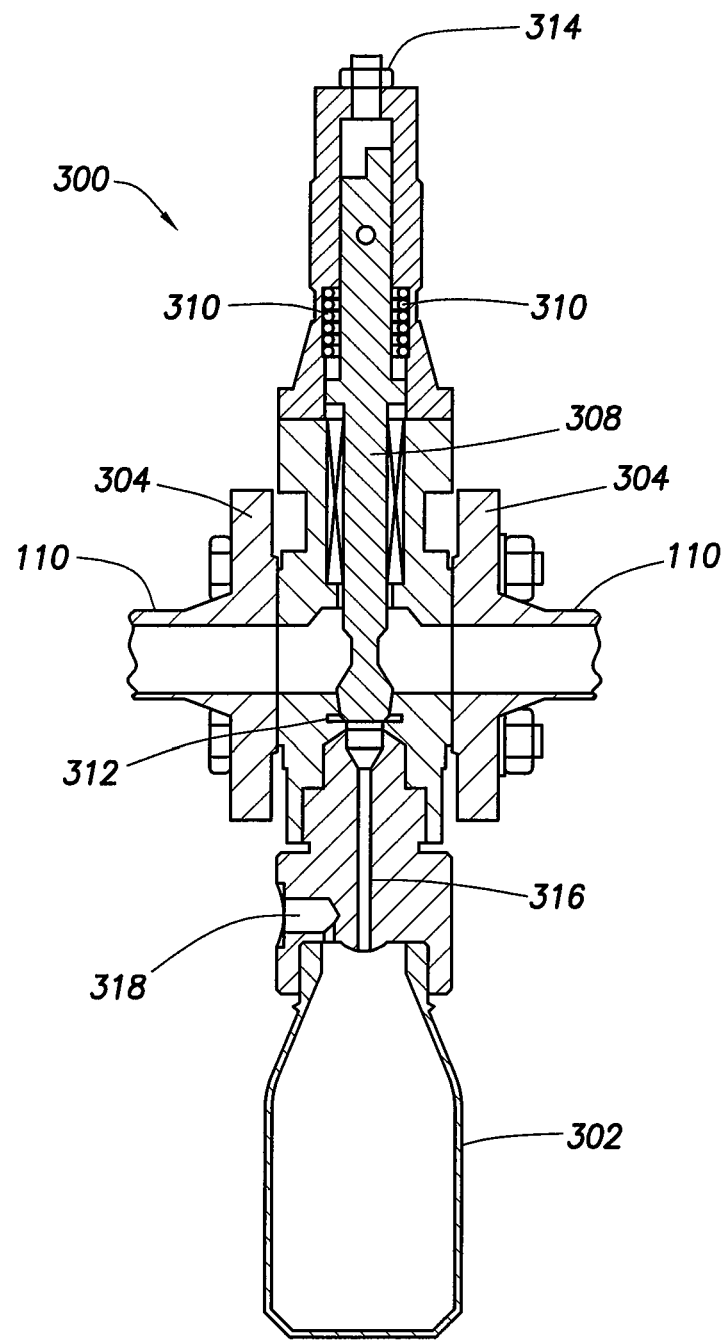
FIG. 3 is an in-line sampling device in the closed position accordance with an embodiment of the present invention.

Shown in FIG. 3 is an in-line sampling device in the closed position in accordance with an embodiment of the present invention denoted generally by reference numeral 300. The in-line sampling device 300 allows fluid samples to be taken directly from the pipe 110 into a sampling container 302. This ensures that a real-time sample is taken from the fluid stream and eliminates sample exposure while eradicating the health and safety risks to personnel who would otherwise be responsible for taking a sample. As would be appreciated by those of ordinary skill in the art, with the benefit of this disclosure, a number of different methods may be used to couple the sampling device 300 with the pipe 110. In one embodiment, the in-line sampling device 300 mounts onto the pipe 110 between two standard flanges 304.

Figure 4:
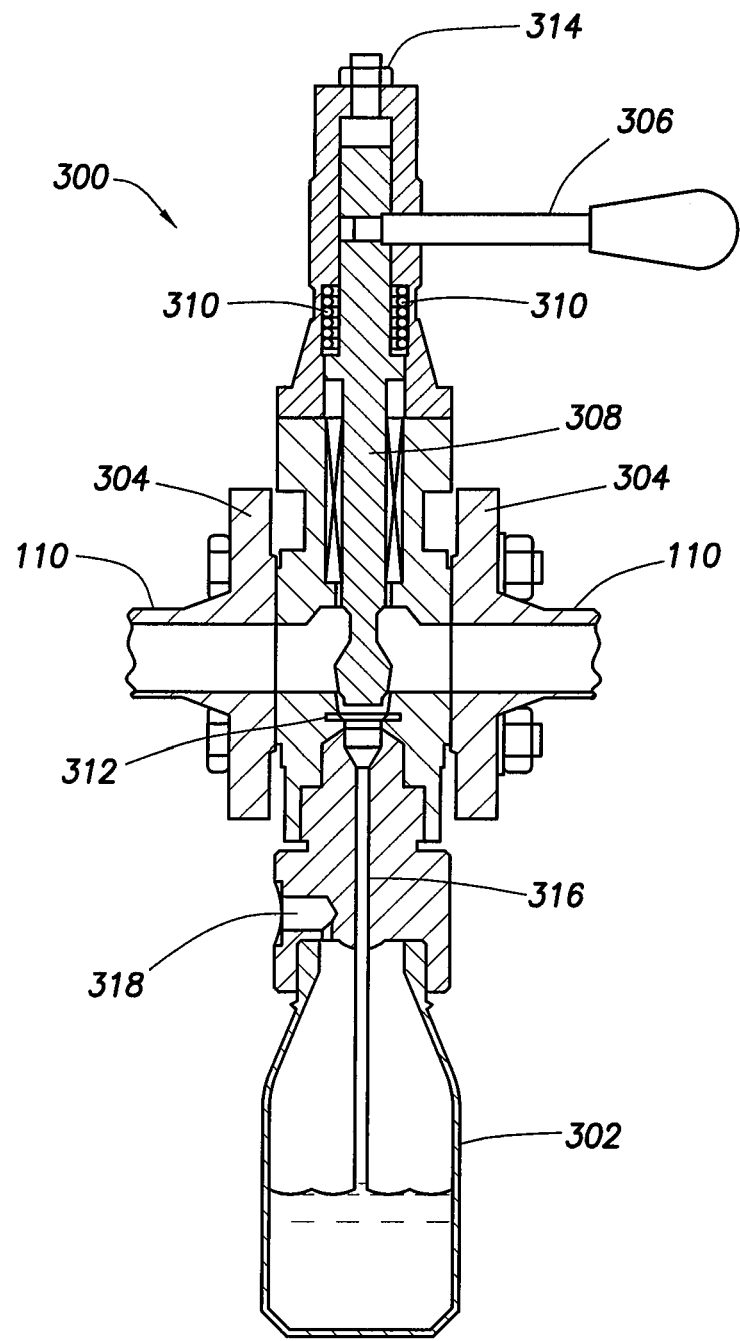
FIG. 4 is an in-line sampling device in the open position in accordance with an embodiment of the present invention.

A sampling container 302 may be coupled at one end of the sampling device 300 and a lever 306 at the other. When a sample is not being taken, a valve spindle 308 may be pressed by a spring 310 against a soft seal 312. Stated otherwise, the spring 310 biases the lever 306 so as to keep the valve spindle 308 pressed against the soft seal 312, thereby keeping the sampling container 302 opening closed. The soft seal 312 is designed to be able to open and close the sampling container. Specifically, the soft seal 312 may be moved into a first position (FIG. 3) where it closes the opening of the sampling container or a second position (FIG. 4) where it opens the opening of the sampling container, allowing fluid to flow therein. FIG. 4 depicts an in-line sampling device in accordance with an embodiment of the present invention in the open position. The lever 306 may be coupled to the valve spindle 308 and used to control the movement of the valve spindle 308, thereby providing a user interface for the operator to control the sampling device 300. Accordingly, the operator may use the lever to control if/when fluid flows into the sampling container 302. Specifically, when it is desirable to obtain a fluid sample, the lever 306 is turned and the valve spindle 308 may be lifted from the soft seal 312. The stroke of the lever 306 can be adjusted by a travel stop 314 to control the rate of fluid flow into the sampling container 302. The valve spindle 308 allows a smooth and controlled sample flow into the sampling container 302 through an inlet 316.

As the sample fills the sampling container 302, any displaced air vents through a ventilation outlet 318. The ventilation outlet 318 may be coupled to a scrubber system when the samples taken include hazardous materials. The operation of scrubber systems is well know to those of ordinary skill in the art and will therefore not be discussed in detail herein.

Although the depicted sampling device 300 utilizes the lever 306, in another exemplary embodiment a multi-turn hand wheel may be used to lift the valve spindle 308. Although a multi-turn hand wheel allows accurate metering of the sample into a container, it is not fail-safe as the operator may mistakenly leave the sample valve open and overflow the sampling container 302. In contrast, in a lever 306 operated design the spring 310 is used to create a spring loaded handle which will automatically close the valve when the operator releases the lever 306 handle. Thus, as would be appreciated by those of ordinary skill in the art, with the benefit of this disclosure, a number of different mechanisms, including, but not limited to, a spring loaded lever, a multi-turn hand wheel, or any other device suitable for opening and/or closing a valve may be used to move the valve spindle 308 and thereby, the soft seal 312 and control the sampling process.

Figure 5:
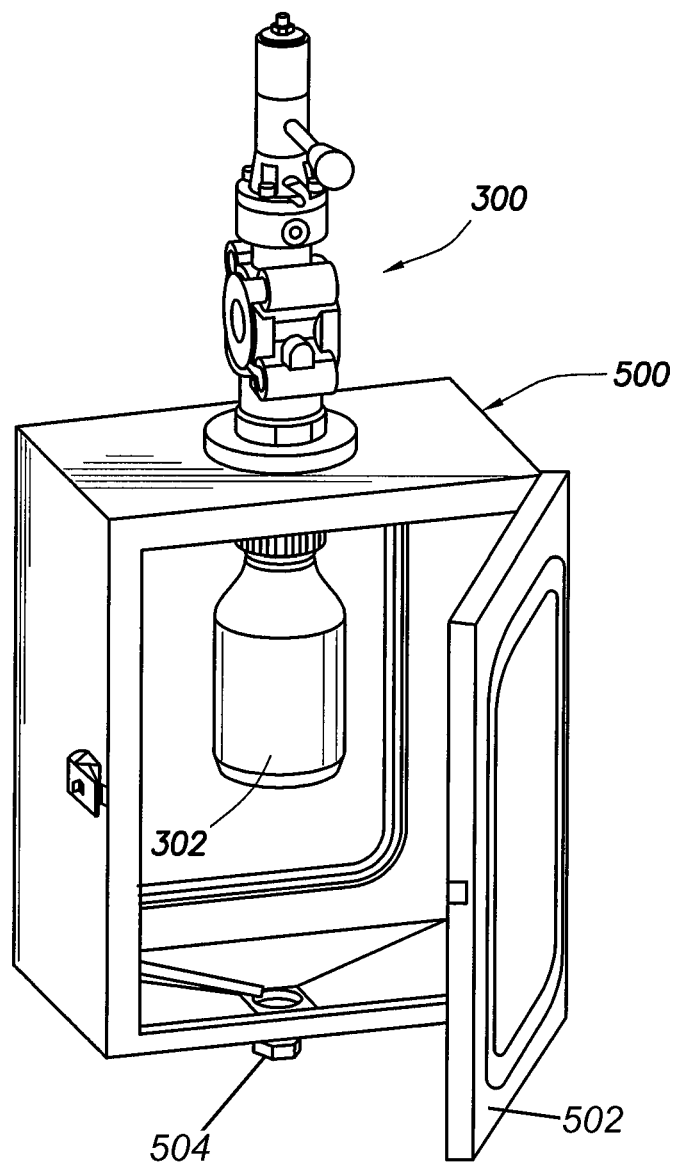
FIG. 5 is a perspective view of a sampling device with a safety enclosure in accordance with an embodiment of the present invention.

Different types of sampling containers 302 may be used in conjunction with the in-line sampling device 300. In one embodiment, the sampling container 302 comprises a glass bottle which is threaded into the bottom of the sample device 300. The bottle will then hold the sample as it is drawn from the pipe 110. In order to minimize sample exposure and the possibility of spills, the sampling container 302 may be enclosed in a box 500 as depicted in FIG. 5. As shown in FIG. 5, the box 500 may include an opening for inserting and removing the sampling container 302 and a door 502 for providing access to the sampling container 302 through that opening. In one exemplary embodiment, the box 500 may further include an opening 504 to allow any materials leaked therein to be drained. Although a box with six sides is depicted in FIG. 5, as would be appreciated by those of ordinary skill in the art, with the benefit of this disclosure, any other suitable means for enclosing the sampling container 302, such as, for example, a spherical enclosure or a cylindrical enclosure may be used as the box 500. In one embodiment, one or more sides of the box 500 may be made of see-through materials, such as, for example, glass, to permit a visual inspection of the sample as it is being obtained. Because the sampling container 302 is placed inside the box 500, it may be capped therein once the sample is obtained, thereby preventing the exposure of the sample taker to any fumes from the sample while minimizing sample exposure to outside elements. The box 500 may be any type of container suitable for containing spills and or fumes. Accordingly, personnel and environmental exposure of the sample is minimized. In another exemplary embodiment, the box 500 may be equipped with an integrated glove compartment (not shown) to permit an operator to detach and cap the sampling container without having to open the door 502.

Computer software may be used to control the mix ratio. The computer software may include a pressure control system, a rate control system, and/or a concentration control system. The pressure control system may control pressure by controlling the pumps 120. The rate control system may control flow rate by controlling the valves 140. The concentration control system may control the concentration by controlling the pumps 120. In one exemplary embodiment, the acid treatment process may be monitored, for instance, by analyzing the sample obtained by the sampling device. The acid treatment progress may then be re-engineered and/or modified while the process is ongoing and a new treatment design may be delivered in real time. In one exemplary embodiment, the operator may obtain a sample for testing using the methods and systems disclosed herein. Based on the results of the analysis of the sample, the operator may program the computer software with new parameters to improve system performance.

The pressure control system may include a drive signal to the centrifugal pumps 120 and feedback from pressure transducers 150. Each of the centrifugal pumps 120 may maintain a separate pressure set point. These pressure set points may be based on expected rate and resultant discharge pressure. The optimal pressure set point may place the valves 140 at a predetermined percentage open for each respective expected rate.

The rate control system may include a drive signal to each valve 140 and feedback from the respective flow meter 160. The valve 140 for a first (or master) component (e.g., water) may be set to 100% open and the rate may be set by the discharge rate, as measured by the discharge flow meter 190. The rate set points for the remaining valves 140 may be set by the concentration control system. Thus, as the requirements for concentrations change (even during a job), the operator has the ability to ramp up or down the concentration and/or liquid additives depending on the specific need. This may be a desirable alternative to the standard practice of mixing a new batch at the acid plant and transporting the mixture to the well site.

The concentration control system may include the rate control system and the rate feedback from the master (e.g., water) rate, which may be measured by the corresponding flow meter 160. Based on a predetermined well treatment fluid mix, the rate set points for the other components may be calculated from a concentration or parts per thousand of the master rate. As the master rate increases, the rate for the other components may also increase. The increasing rate of other components will slow the increasing master rate until the desired concentration is established.

The system 100 may optionally include additional components. For example, as shown in FIG. 1, the system 100 may include a tank 192. Due to the nature of the types of chemicals used, the tank 192 may be situated on the discharge side of the system 100. The tank 192 may be used to prevent loss if something goes wrong and the job must be stopped. Additionally, the tank 192 may be useful in situations where the flow rates are very low. As would be appreciated by those of ordinary skill in the art, with the benefit of this disclosure, additional valves 196 may be used to control the flow of the fluid through the tank 192. For example, these additional valves may be butterfly valves, some of which are open and some of which are closed.

This system 100 may be used for acid blending for acidizing wells, otherwise known as "Acid-On-the-Fly," which involves blending two or more major hazardous chemical components into a pressurized piping system and injecting one or more liquid additives into that flow stream. This system 100 may alternatively be used for fracturing operations, in which case the treatment fluid would be a fracturing fluid. Additionally, this system 100 may be used for drilling operations, in which case the treatment fluid would be drilling mud. Therefore, although the present invention is described in the context of acids, as would be appreciated by those of ordinary skill in the art, with the benefit of this disclosure, the system and methods of the present invention may also apply to non-acids or other material requiring high-shear preparation on a single pass such as on-location preparation of emulsion based fracturing fluids, completion fluids, cementing fluids such as spacers, and drilling fluids.

The ability to blend "On-the-Fly" may reduce the amount of blended chemicals requiring disposal upon completion of the process. It may also lower exposure of hazardous chemicals to personnel and the environment. Furthermore, it may decrease the number of personnel required for the process and decrease the amount of time hazardous chemicals would be in use. Additionally, by blending the chemicals as they are pumped downhole, there may be a significant reduction of waste that must be disposed of, and cost associated with that disposal process. Further, there may be a reduction in cost for transporting the mixed chemicals, since that would no longer be a requirement. Additionally, there may be a reduction of cost for buying and maintaining the highly regulated cargo tank motor vehicles. Additionally, there may be a reduction and/or elimination of the bulk chemical plants (otherwise known as acid plants) currently being used. By eliminating bulk acid plants, transports, and the physical handling of these types of chemicals, the risk of personal and environmental exposure may be significantly reduced.

In one exemplary embodiment, the one or more pumps used in the system may be graphite pumps. As would be appreciated by those of ordinary skill in the art, with the benefit of this disclosure, graphite is used as an illustrative example and the one or more pumps may be made of any other suitable material that is inert to chemical exposure. Using such inert materials allows a variety of corrosive fluids to be pumped, including sources of HF acid, strong HCL acid, and many solvents that would damage conventional delivery pumps. Moreover, the system disclosed herein may be equipped with a "kill switch" that can terminate the operations in case of an emergency.

In one exemplary embodiment, the system disclosed herein may be mounted onto a trailer that can be easily transported from one job site to another. Moreover, as would be appreciated by those of ordinary skill in the art, with the benefit of this disclosure, because the acid mixture is made on the fly, as needed, there is no residue acid at the end of the well treatment operations that needs to be disposed. Accordingly, the components of the well treatment fluid that are unused may be saved for another well treatment operations and the environmental and operations costs associated with disposing of the unused acid mixture are eliminated.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In addition, the terms in the claims have their plain, ordinary meaning unless otherwise explicitly and clearly defined by the patentee.

What is claimed is:

1. A method for blending a well treatment fluid at a well site, comprising:
   providing a first centrifugal pump for pumping a first component of the well treatment fluid into a pipe;
   providing a first valve for controlling the flow of the first component of the well treatment fluid into the pipe;
   providing a second centrifugal pump for pumping a second component of the well treatment fluid into the pipe;
   providing a second valve for controlling the flow of the second component of the well treatment fluid into the pipe;
   controlling one or more of the first centrifugal pump, the first valve, the second centrifugal pump and the second valve so as to control a ratio of the first component of the well treatment fluid to the second component of the well treatment fluid being delivered to the pipe, wherein controlling one or more of the first centrifugal pump, the first valve, the second centrifugal pump and the second valve further comprises:
      adjusting, if the difference between the discharge pressure of the first centrifugal pump and the discharge pressure of the second centrifugal pump exceeds a predetermined balance, an operating parameter of at least one of the first centrifugal pump, the second centrifugal pump, the first valve, and the second valve;
   wherein the first component of the well treatment fluid and the second component of the well treatment fluid are mixed in the pipe; and
   providing a sampling device for analyzing the well treatment fluid flowing in the pipe, wherein the sampling device comprises:
      a sampling container;
      a soft seal movable between a first position and a second position, wherein the soft seal closes an opening of the sampling container when in the first position and opens the opening of the sampling container when in the second position; and a valve spindle, wherein the valve spindle moves the soft seal between the first position and the second position.

2. The method of claim 1, wherein the sampling device further comprises a lever coupled to the valve spindle, wherein the lever controls movement of the valve spindle.

3. The method of claim 2, wherein the sampling device further comprises a spring, wherein the spring biases the lever to maintain the soft seal in the first position.

4. The method of claim 1, further comprising enclosing the sampling container in a box.

5. The method of claim 1, wherein the sampling device further comprises a ventilation outlet, wherein air displaced from the sampling container flows out through the ventilation outlet.

6. The method of claim 1, further comprising:
providing at least one liquid additive storage tank;
providing at least one liquid additive pump; and
providing at least one liquid additive valve for controlling the flow of liquid additive into the pipe;
wherein controlling the liquid additive pump and the liquid additive valve controls a ratio of the liquid additive to at least one of the first component of the well treatment fluid and the second component of the well treatment fluid.

7. The method of claim 6, further comprising: pumping the well treatment fluid from the pipe into a well.

8. The method of claim 1, wherein the well treatment fluid is a fracturing fluid.

9. The method of claim 1, wherein the well treatment fluid is a drilling mud.

10. A system for blending a well treatment fluid at a well site, comprising:
a first centrifugal pump for pumping a first component of the well treatment fluid into a pipe;
a first valve for controlling the flow of the first component of the well treatment fluid into the pipe;
a second centrifugal pump for pumping a second component of the well treatment fluid into the pipe;
a second valve for controlling the flow of the second component of the well treatment fluid into the pipe;
a controller for adjusting, if the difference between the discharge pressure of the first centrifugal pump and the discharge pressure of the second centrifugal pump exceeds a predetermined balance, an operating parameter of at least one of the first centrifugal pump, the second centrifugal pump, the first valve, and the second valve;
wherein one or more of the first centrifugal pump, the first valve, the second centrifugal pump and the second valve control a ratio of the first component of the well treatment fluid to the second component of the well treatment fluid being delivered to the pipe;
wherein the first component of the well treatment fluid and the second component of the well treatment fluid are mixed in the pipe; and
a sampling device coupled to the pipe, wherein the sampling device comprises:
a sampling container;
a soft seal movable between a first position and a second position, wherein the soft seal closes an opening of the sampling container when in the first position and opens the opening of the sampling container when in the second position; and
a valve spindle, wherein the valve spindle moves the soft seal between the first position and the second position.

11. The system of claim 10, wherein valve spindle is movable using a mechanism selected from a group consisting of a spring loaded lever and a multi-turn hand wheel.

12. The system of claim 10, wherein the sampling container is enclosed in a box.

13. The system of claim 10, wherein the sampling device further comprises a ventilation outlet, wherein air displaced from the sampling container flows out through the ventilation outlet.

14. The system of claim 11, wherein the ventilation outlet is coupled to a scrubber system.

15. The system of claim 10, further comprising:
at least one liquid additive storage tank;
at least one liquid additive pump; and
at least one liquid additive valve for controlling the flow of liquid additive into the pipe;
means for controlling the liquid additive pump and the liquid additive valve so as to control a ratio of the liquid additive to at least one of the first component of the well treatment fluid and the second component of the well treatment fluid.

16. The system of claim 15, further comprising a pump, wherein the pump pumps the well treatment fluid from the pipe into a well.

17. The system of claim 10,
wherein the well treatment fluid is an acidizing fluid; and
wherein the first component of the well treatment fluid is water.

18. The system of claim 17, wherein the second component of the well treatment fluid is Ammonium Bi-Fluoride.

19. The system of claim 18, wherein the well treatment fluid comprises a third component and wherein the third component of the well treatment fluid is hydrochloric acid.

20. The system of claim 10, wherein the well treatment fluid is one of a fracturing fluid or a drilling mud.

* * * * *